United States Patent [19]
Brenner

[11] Patent Number: 5,807,683
[45] Date of Patent: Sep. 15, 1998

[54] COMBINATORIAL LIBRARIES AND METHODS FOR THEIR USE

[75] Inventor: Sydney Brenner, Cambridge, England

[73] Assignee: CombiChem, Inc., San Diego, Calif.

[21] Appl. No.: 281,195

[22] Filed: Jul. 26, 1994

Related U.S. Application Data

[63] Continuation-in-part of Ser. No. 168,966, Dec. 15, 1993, abandoned, which is a continuation of Ser. No. 978,646, Nov. 19, 1992, abandoned.

[51] Int. Cl.⁶ .................................................... G01N 33/53
[52] U.S. Cl. ........................... 435/7.1; 436/501; 436/518; 436/528; 436/531
[58] Field of Search ........................ 435/6, 7.1; 436/501, 436/518, 528, 531; 530/334

[56] References Cited

U.S. PATENT DOCUMENTS

| | | | |
|---|---|---|---|
| 5,010,175 | 4/1991 | Rutter et al. ............................. | 530/334 |
| 5,182,366 | 1/1993 | Huebner et al. ......................... | 530/334 |
| 5,288,514 | 2/1994 | Ellman ......................................... | 427/2 |
| 5,541,061 | 7/1996 | Fodor et al. ................................. | 435/6 |

FOREIGN PATENT DOCUMENTS

| | | |
|---|---|---|
| 8600991 | 2/1986 | WIPO . |
| 9119818 | 12/1991 | WIPO . |
| 9200091 | 1/1992 | WIPO . |
| 9209300 | 6/1992 | WIPO . |
| 9306121 | 4/1993 | WIPO . |
| 9309668 | 5/1993 | WIPO . |

OTHER PUBLICATIONS

Furka et al "More Peptides by Less Labow" Eur. Fed. Med. Chem., 8th International Symposium on Med. Chem. p.–168 (1988).

Greysen, et al., Use of peptide synthesis to probe viral antigens for epitopes to a resolution of a single amino acid, *Proc. Natl. Acad. Sci. USA*, vol. 81, pp. 3998–4002, Jul. 1984.

Lam et al., A new type of synthetic peptide library for identifying ligand–binding activity, Nature, vol. 354, 7 Nov. 1991, pp. 82–84.

Houghten et al., Generation and use of synthetic peptide combinatorial libraries for basic research and drug discovery, Nature, vol. 354, 7 Nov. 1991, pp. 84–86.

*Primary Examiner*—Lora M. Green
*Attorney, Agent, or Firm*—Townsend and Townsend and Crew LLP; Lorie Ann Morgan

[57] ABSTRACT

Kit, and method for its use and construction, which includes a first plurality of vessels containing different polysubunits, each constructed from a known number of subunits. Each subunit is joined by one or more bonds and each subunit and bond can be the same or different. Each of the different polysubunits has a different sequence of subunits but has the same known subunit at one terminus. Each vessel contains polysubunits which have a different known subunit at one terminus. The kit further includes a second plurality of vessels which includes different polysubunits, each constructed from the known number minus one subunit, as described above.

5 Claims, 4 Drawing Sheets

COMBINATORIAL LIBRARIES AND METHODS FOR THEIR USE

This application is a continuation-in-part of U.S. application Ser. No. 08/168,966, filed Dec. 15, 1993, now abandoned which is a continuation of U.S. application Ser. No. 07/978,646, filed Nov. 19, 1992 now abandoned.

BACKGROUND OF THE INVENTION

This invention relates to synthetic combinatorial libraries useful for drug discovery, and methods for their use in such drug discovery.

Houghten et al., 354 Nature 84, 1991 and WO 92/09300 (PCT/U.S. Ser. No. 91/08694), describe the generation and use of synthetic peptide combinatorial libraries for basic research and drug discovery. These libraries are composed of mixtures of free peptides which form a heterogenous library. Systematic identification of optimal peptide ligands is achieved by screening a library followed by iterative selection and synthesis processes. For example, one library consisted of a series of six residue peptides having the first two positions specifically defined, and the last four positions consisting of a random mixture of 18 L-amino acids. This library was screened to determine which pair of defined peptides had optimum activity in an assay. A second library was then synthesized in which the optimal pair of peptides were included, the third position of each peptide individually synthesized, and the last three peptides consisted of a random mixture of 18 L-amino acids. This library was screened as before and the process repeated until the optimum six residue peptide was identified. Houghten et al. state:

"A number of other libraries, such as one composed entirely of D-amino acids, have been prepared which in total permit the systematic screening of hundreds of millions of peptides. A fundamental feature of SPCLs [synthetic peptide combinatorial libraries] is that free peptides can be generated and used in solution in virtually all existing assay systems at a concentration of each peptide most applicable to the assay. This approach has also been successfully used in radio-receptor assays (opioid peptides) and plaque inhibition assays (human immunodeficiency virus (HIV-1) and Herpes Simplex Virus (HSV)). SPCLs, as described, greatly aid all areas of drug discovery and research involving peptides."

Lam et al., 354 Nature 82, 1991, and WO 92/00091 (PCT/U.S. Ser. No. 91/04666) and Houghten et al., 354 Nature 84, 1991 and WO 92/09300 (PCT/U.S. Ser. No. 91/08694), describe systematic synthesis and screening of peptide and other libraries of defined structure. The method used by Lam et al. is based on a one bead one peptide approach in which a large peptide library consisting of millions of beads are screened. Each bead contains a single peptide. The authors state:

"It is clearly not enough to use a random mixture of activated amino acids in a peptide synthesis protocol, because the widely different coupling rates of different amino acids will lead to unequal representation and because each bead will contain a mixture of different peptides. Our solution was to use a 'split synthesis' approach. The first cycle consisted of distributing a pool of resin beads into separate reaction vessels each with a single amino acid, allowing the coupling reactions to go to completion, and then repooling the beads. The cycle was repeated several times to extend the peptide chain. In this fashion, each bead should contain only a single peptide species."

The library of beads was screened by a staining procedure and stained beads visualized using a microscope, and removed. The structure of the peptide is obtained by a chemical analysis of the material on the single bead. Lam et al. indicate:

"Additionally, our approach has far greater potential for applying the richness of well-established peptide chemistry to synthesize libraries incorporated D-amino acids or unnatural amino acids as well as specific secondary structures including cyclic peptides.

All of this can be accomplished without need to keep records of the synthetic products as our interest is focused just on those peptides which provide a strong interaction signal with the acceptor."

SUMMARY OF THE INVENTION

The present invention features an efficient method for the construction and decomposition of combinatorial libraries to allow identification of useful polysubunit compounds (made up from two or more subunits which may be the same or different, referred to sometimes as polymers). The method is not limited to identification of polypeptides; it can be applied to any combination of compounds made up of differing subunits (referred to sometimes as monomeric compounds) within one polysubunit compound. Synthesis of such polysubunits can be carried out chemically or with the use of catalysts, including enzymes. Thus, for example, the subunits may be selected from natural or unnatural moieties, including amino acids, nucleotides, sugars, lipids, and carbohydrates. In addition, the bond used to attach each subunit to the prior subunit can make any desired type of bond, and may include covalent, ionic or coordination bonds. The bonds may be selectively cleavable by enzymes or chemical treatments, as desired. Examples of such bonds include: peptide [$R^1CONHR^2$], ester [$R^1COOR^2$], sulfonamide [$R^1SO_2NR^2$], thioester [$R^1COSR^2$], phosphodiester [$R^1OPOR^2$], ether [$R^1COCR^2$], thioether [$R^1CSCR^2$], phosphamide [$R^1PONH$-], amine [—$CH_2NHC$—], and azo [—CNNC—] (where each $R^1$ and $R^2$ may be the same or different and may be cyclic or acyclic). In the method, a free or solid-phase-bound polysubunit can be used to allow ready screening of the synthesized polysubunits in any desired test or assay system. A significant advantage of this invention is that it provides a series of libraries or collections of polysubunits which can be reused for screening for any number of desired properties in any chosen assays.

The present method does not employ a mixed synthesis in which several different subunits are chemically incorporated within one vessel, but rather a synthesis in which a single subunit is incorporated at each step. See FIG. 1.

Figure 1:
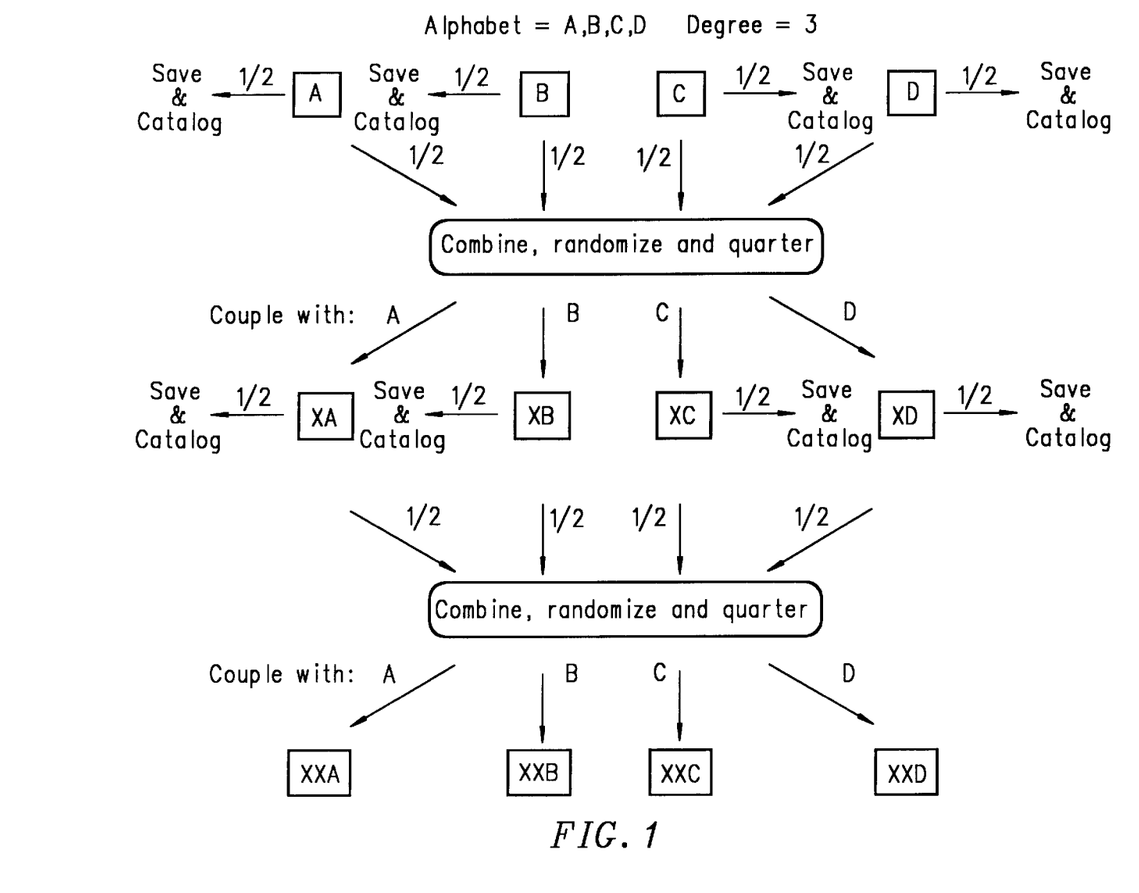
FIG. 1 illustrates split pool synthesis of a combinatorial library.

Thus, in one example, the method involves a first step of attaching ten different subunits A, B, C . . . J, to a solid support in ten separate vessels or columns. In the second step, a portion or aliquot of the material synthesized at the first step is retained as separate columns, while the remainder (which is still attached to individual solid supports) is mixed or pooled, divided into ten new different columns, and ten further parallel syntheses carried out to provide the dimer $XA^1$, $XB^1$, $XC^1$ . . . $XJ^1$, where X is any one of the original A–J, and $A^1$, $B^1$, $C^1$ . . . $J^1$ are ten different subunits which may be the same or different from A–J. Of course, fewer or more than ten syntheses can be used in this second step. In the third step, a portion of the newly synthesized material of step two is again retained in separate columns, and the remainder mixed and divided into ten further columns so that the synthetic procedure can be repeated until the whole length of the desired polysubunit is synthesized. In this way a series of vessels is formed at each step, differing from those in prior steps by the presence of an extra subunit.

Figure 2:
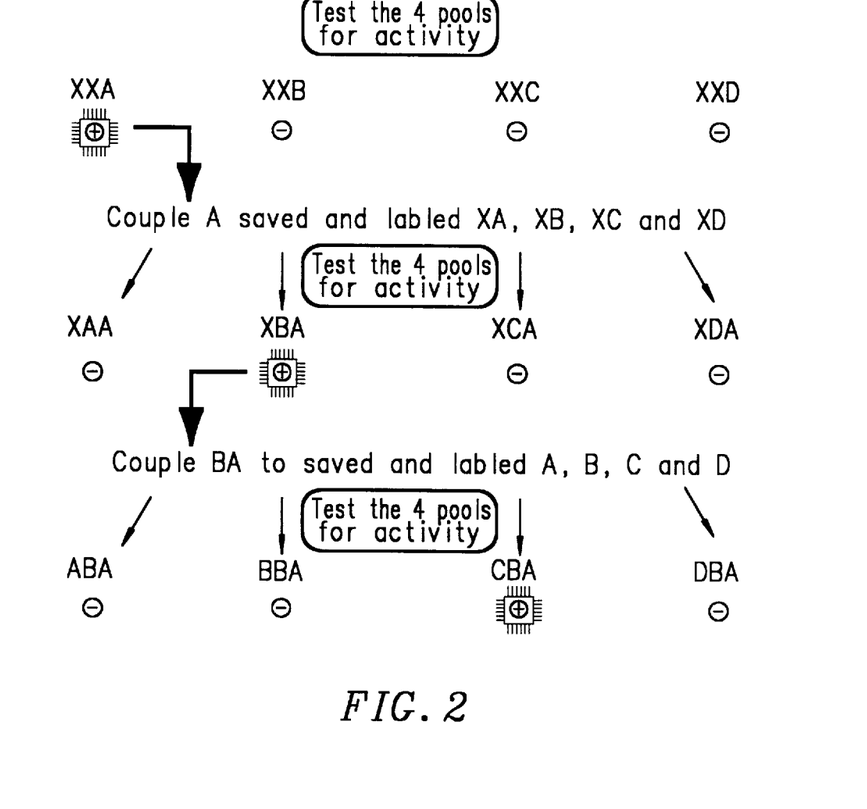
FIG. 2 illustrates utilization of the deconvolution pathway to determine the sequence of a member of a combinatorial library.

The final ten columns in the above example (each having a variety of different polysubunits with a known subunit at their terminus) can be assayed using any standard assay format. That is, each of the ten mixtures is assayed to determine which mixture contains one or more active compounds. The column which is found to contain an active compound identifies the subunit required at the polysubunit terminus to be active in the assay. For example, the column containing polysubunits of sequence XXXXJ$^1$ may be active in the assay. This indicates that J$^1$ is required at the terminus of a polysubunit in this assay. This subunit is now bonded to each of the columns retained in the previous synthetic step (in the example, the columns XXXA, XXXB, . . . XXXJ). These ten newly synthesized series of compounds can then be assayed and the process repeated until the final polysubunit sequence is known. See FIGS. 2 and 3.

Thus, the method of the present invention features a set or kit of partial combinatorial libraries with each library containing one subunit more than the prior library. The final library is decomposed stepwise starting with the last subunit. This form of retroanalysis or antithesis allows definition of the synthesis of the desired product, which is accomplished in the final analytic step. Once constructed, the entire set of libraries can be used for many different projects.

Thus, in a first aspect, the invention features a kit which includes a first plurality of vessels containing different polysubunits, each constructed from a known number of subunits. Each subunit is joined by one or more bonds, and each subunit and bond can be the same or different. Each of the different polysubunits has a different sequence of subunits, but has the same known subunit at one terminus. Each vessel contains polysubunits which have a different known subunit at their terminus. The kit further includes a second plurality of vessels which includes different polysubunits, each constructed from the known number minus one subunit, as described above.

This kit forms a combinatorial library which can be screened and decomposed as discussed above. The number of first and second pluralities of vessels can be the same or different, and generally the terminus of the polysubunits to which subunits are added is the same in each set of vessels.

In preferred embodiments, the kit may include further pluralities of vessels in which the number of subunits present in the polysubunit is the known number minus two, or three, or more. Thus, each plurality of vessels differs from other pluralities of vessels in the number of subunits present in the polysubunits. Most preferably, the number of subunits in each plurality of vessels differs by one and ranges from one to the known number. As discussed above, such a kit is useful for systematic identification of the sequence of a desired polysubunit, using the method of retroanalysis.

As noted above, the polysubunits may be formed from any series of subunits desired, and the number of vessels containing these polysubunits at each step can be different for each subunit added. Thus, as described above, ten amino acids may be incorporated in one step, two or three carbohydrates may be incorporated in another step, and twenty amino acids in the following step. There is no limit to the steps of addition of subunits, nor to the choice of subunits which can be added at each step. All that is necessary for the kit to be useful is that the kit include a series of vessels which contain polysubunits differing sequentially in the number of subunits present in those polysubunits. The final plurality of vessels in the kit will contain only the first subunit free in solution, or bound to a solid support.

In a related aspect the invention features, a method for construction of a kit, following the steps described above, and a method for screening such kits as described above.

Specifically, the invention features a method for construction of a kit useful for identification of a desired compound, by the steps of: (a) providing a first plurality of vessels containing different polysubunits each constructed from a known number of subunits joined together by one or more bonds. Each subunit and bond can be the same or different, and each different polysubunit has a different sequence of subunits but the same known subunit at one terminus of the polysubunit. Each vessel includes polysubunits having a different known subunit at their terminus; (b) combining aliquots of the different polysubunits from each vessel to form a mixture; wherein the aliquots are less than all of the contents of each vessel; (c) dividing the mixture into a second plurality of vessels; and (d) bonding a further subunit to each polysubunit in the second plurality of vessels; wherein the subunit is different for each second plurality of vessels.

In preferred embodiments, the method further includes repeating steps (a) through (d) for the second plurality of vessels; or repeating steps (a) through (d) a plurality of times.

In a related aspect, the invention features a method for identification of a desired compound, including the steps of: (a) providing a kit as described above, and screening the first plurality of vessels to identify a vessel having a desired activity in an assay, and thereby identifying a first known subunit; and (b) coupling the first known subunit to a terminus of an aliquot of the contents of each of the different polysubunits in the second plurality of vessels.

In preferred embodiments, the method further involves screening the different polysubunits having the first known subunit for the desired activity in the assay, and thereby identifying a second known subunit; or repeating steps (a) and (b) a plurality of times.

Other features and advantages of the invention will be apparent from the following description of the preferred embodiments thereof, and from the claims.

DESCRIPTION OF THE PREFERRED EMBODIMENTS

The drawings will first briefly be described.
Drawings.

Applicant has determined that a useful series, or kit, of libraries can be constructed by stepwise synthesis of a polysubunit from different subunits. While these libraries and methods for their synthesis and use will commonly be applied for use with peptides formed from standard L- or D-amino acids, those of ordinary skill in the art will recognize that other subunits and bonds other than covalent, ionic or coordination bonds can be used to form the final polysubunit, which can then be screened in any standard assay. These synthetic protocols and assays are well known to those of ordinary skill in the art and need not be repeated here. See, Lam et al., supra, and Houghten et al., supra, the whole of all of which are hereby incorporated by reference herein. As an illustrative example of a method and kit of this invention, the following is provided. This example is not limiting in the invention and those of ordinary skill will realize (as noted above) that other equivalent methods, syntheses, and analyses can be readily used.

EXAMPLE

The method proposed here is based on a true combinatorial synthesis and makes efficient use of all of the materials. The first step is to attach ten subunits, A to J, to a solid support in ten columns. One-sixth of this material is retained in this form, giving A, B, . . . J; the remainder, still attached to the solid support, is pooled, divided into ten columns, and ten parallel syntheses are carried out, to provide XA, XB, . . . XJ. One-fifth of this material is retained in this form, and the combinatorial synthesis is repeated to give ten polysubunits, XXA, XXB, . . . XXJ. One-fourth is kept and the fourth residue is added to the remainder by combinatorial synthesis to give the polysubunits XXXA, XXXB, . . . XXXJ. After retaining one-third of these polysubunits the final combinatorial step of synthesis is completed, and the materials are removed from the column to provide ten solutions containing XXXXA, XXXXB, XXXXJ. These are now assayed.

If a positive assay result is obtained with one vessel containing polysubunits of the structure XXXXC (i.e., C is the critical subunit at the fifth position in the pentasubunit), the experimenter returns to the columns retained at the previous step, and to an aliquot of each adds C, to provide ten solutions, XXXAC, XXXBC . . . XXXJC. Again, these are tested. If a positive assay result is obtained with XXXEC (i.e., E is the critical subunit at position four in the pentasubunit), the experimenter returns to the previous partial library and completes it by adding E+C to all ten to give XXAEC, XXBEC . . . XXJEC. These steps are repeated until all of the positions are specified.

Thus, in essence a set of partial combinatorial libraries is made, each one residue longer than the last. The final library is decomposed stepwise, starting with the last residue. This form of retro-analysis allows definition of the synthesis of the desired product, which is indeed accomplished in the very last step. Once constructed, the entire set of libraries can be used again for different projects.

It is notable that the final synthetic step also provides a method for synthesis of the desired product.

Materials and Methods

Solvents

DMF (HPLC grade) was purchased from Baxter and was used without further purification. $CH_2Cl_2$ was purchased from Fisher Scientific and was distilled over $CaH_2$ before use.

Instrumentation

UV absorbances were measured on a Hewlett-Packard 8452A diode array spectrophotometer. All centrifugations were carried out on an Eppendorf 5415 C centrifuge for one minute at 10,000 rpm.

Formation of the Pentapeptide Library

The peptide libraries were synthesized manually by a solid phase method. Tentagel (TG) resin was the solid support for all synthesis and was 90 Mm in diameter. The amino acids used for the formation of the libraries were Gly-FMOC, Leu-FMOC, Phe-FMOC and Tyr(tBu)-FMOC. All amino acids were coupled with the aid of HBTU and DIPEA. The Tentagel, HBTU, DIPEA and amino acids used were purchased from NovaBiochem. Tentagel was added to 4 glass fritted filter vials, shaken with DMF and filtered. To each vial was added one of the FMOC protected amino acid components of the library, HBTU, DMF and 20 µl DIPEA. All four vials were shaken for one hour, filtered and washed with DMF. A 5% solution (v/v) of acetic anhydride in DMF was added to each vial and shaken for 20 minutes to cap any uncoupled free amino acid groups. The beads were then filtered, washed with DMF (2×) and $CH_2Cl_2$ (2×) and dried for two hours in a vacuum oven (55° C. at 20 mm Hg). Approximately, a 75 mg portion of the amino acid coupled Tentagel bead was taken from each vial and labeled in a manner describing the length of the peptide and the identity of the last amino acid coupled. Also, an approximately 5 mg portion of the resin was taken to do an FMOC deprotection test in order to quantitate the completeness of the previous amino acid coupling step. The remaining resin was combined and shaken in 3:1 (v/v) DMF/$CH_2Cl_2$ for 30 minutes to randomize the beads. The beads were quartered into equivalent weight (and therefore equivalent moles) and set into 4 glass fritted filter vials and subjected twice to 10 minute shakings with 20% Piperidine in DMF (v/v) in order to cleave the N-terminal FMOC protecting group. The beads were filtered, washed with DMF (3×) and coupled with one of the 4 amino acid components of the library to give the 4 dipeptide pools, TG-Xaa-Gly-FMOC, TG-Xaa-Leu-FMOC, TG-Xaa-Phe-FMOC, and TG-Xaa-Tyr(tBu)-FMOC. The steps of 1) capping the peptide with acetic anhydride, 2) saving and labeling a 75 mg portion of the resin, 3) combining, randomizing and evenly dividing the beads and 4) coupling each division with an FMOC protected amino acid was repeated until the 5th coupling. At this point there are 4 pentapeptide libraries. These pentapeptide libraries were cleaved of the t-butyl protecting group on the tyrosines by mixing the resin with TFA (Pierce) for 2 hours. The beads were filtered and washed with ethanol (2×) and DMF (2×). The beads were then shaken with 20% Piperidine in DMF (v/v) twice for 10 minutes to cleave the N-terminal FMOC group. The deprotected beads were then washed with DMF (3×), $CH_2Cl_2$ (2×) and set in a vacuum oven overnight (55° C. at 20 mm Hg) to evaporate any residual solvent.

ELISA Procedure

The library containing Tentagel resin (~3 mg) was added to a polypropylene tube. The tube was coated with a 1:1 (v/v) blocking solution of 3% BSA in PBS (w/v) and 0.05% Tween-20 (Sigma) in PBS (v/v). The tube was incubated with 500 µl of a 1:1:1 (v/v/v) solution consisting of 1 µg/ml mouse anti-β-endorphin monoclonal antibody (Boehringer Mannheim) in PBS, 3% BSA in PBS and 0.05% Tween-20 in PBS at 37° C. for one hour. The tube was centrifuged and the supernatant was decanted. The tube was washed 3 times by repetitively adding 0.05% Tween-20 in PBS, centrifuging the tube and decanting the supernatant. The tube was then incubated with 500 µl of goat anti-mouse antibody conjugated to glucose oxidase (from Cappel, diluted by a factor of 1000 with a 1:1 (v/v) solution of 3% BSA in PBS and 0.05% Tween-20 in PBS). The tube was washed 3 times by repetitively adding 0.05% Tween-20 in PBS, centrifuging the tube and decanting the supernatant and 2 times by adding PBS, centrifuging the tube and decanting the supernatant.

A developing solution containing 25 ml of 0.1M $Na_3PO_4$ (pH 6.0), 3 ml of 20% glucose in $H_2O$, 200 μl horseradish peroxidase (0.1% in 0.1M $Na_3PO_4$, pH 6.0) and 200 μl ABTS dye (45 mg/ml in 0.1M $Na_3PO_4$, pH 6.0) was prepared. A 500 μl aliquot of the developing solution was added to the tube and allowed one hour to react with the peptide library before UV readings were taken. For the UV measurements of the assay, 900 μl of 0.1M $Na_3PO_4$ (pH 6.0) was placed in a cuvette and measured as the blank, 100 μl of the developed solution was then introduced to the cuvette and the UV absorbance at 416 nm was monitored.

Data Analysis

For each ELISA, besides assaying the pentapeptide libraries, a positive and negative control were also simultaneously assayed. The positive control was the independently synthesized pentapeptide, TG-Leu-Phe-Gly-Gly-Tyr-$NH_2$. The negative control was acetylated Tentagel (TG-Ac). The measured UV absorbance was normalized, to take into account the weight differences of the TG-resin in each assay tube, to give a normalized absorbance. The normalization was calculated by multiplying the measured absorbance at 416 nm by the mass of the material in the TG-Ac (negative control) assay tube. This product was divided by the mass of the TG-resin in the pentapeptide library tube to give the normalized absorbance. The absorbance of the negative control was subtracted from the normalized absorbance to give a corrected absorbance.

In the early stages of the deconvolution, the negative control gave higher absorbance readings than some of the libraries. This accounts for the sub-zero absorbances seen on the graphs. As the library became more defined, fewer negative corrected absorbances were obtained.

Quantification of Amino Acid Coupling

A standard solution was prepared by adding DMF to a known amount of Gly-FMOC to a volume of 100 ml. 980 μl of 20% piperidine in DMF (v/v) was scanned as a blank. 20 μl of the Gly-FMOC solution was added to the blank, swirled for 5 minutes and scanned. The piperidine-benzofulvene complex that forms upon cleavage of the FMOC group by piperidine has a diagnostic UV absorbance peak at 302 nm. After the coupling, capping and drying steps of the combinatorial library synthesis, a determination of the completeness of each coupling was performed by taking a known mass of Tentagel resin (usually ~5 mg) from each reaction vial and placing the sample in a 1 dram vial. The vials containing the resin samples were shaken with 1000 μl of 20% piperidine in DMF for 15 minutes. The resin was allowed to settle to the bottom and 100 μl of the piperidine treated resin solution was added to 900 μl of 20% piperidine in DMF which was previously added to a cuvette and scanned as a blank. The UV absorbance at 302 nm was compared to the standard to quantitate the extent of the amino acid coupling.

As a simple test of our method of deconvolution, an experiment was devised which screened libraries containing the well studied pentapeptide sequence, Leu-Phe-Gly-Gly-Tyr-$NH_2$, which displays nanomolar binding to commercially available anti-β-endorphin monoclonal antibody. A synthetic combinatorial peptide library with a degree of 5 and an alphabet consisting of leucine, glycine, phenylalanine and tyrosine, was synthesized on Tentagel solid support. The total number of molecules in this library is $4^5$ (1024 members).

The coupling of the FMOC protected amino acids to the solid support with HBTU proceeded smoothly and quantitatively, according to FMOC cleavage measurements taken after each coupling. The quantitativeness of the coupling is advantageous since we can assume that the loading capacity (and therefore the number of moles per gram of resin) is approximately constant, no matter at what stage we are at in the synthesis or deconvolution of the library.

Figure 3:
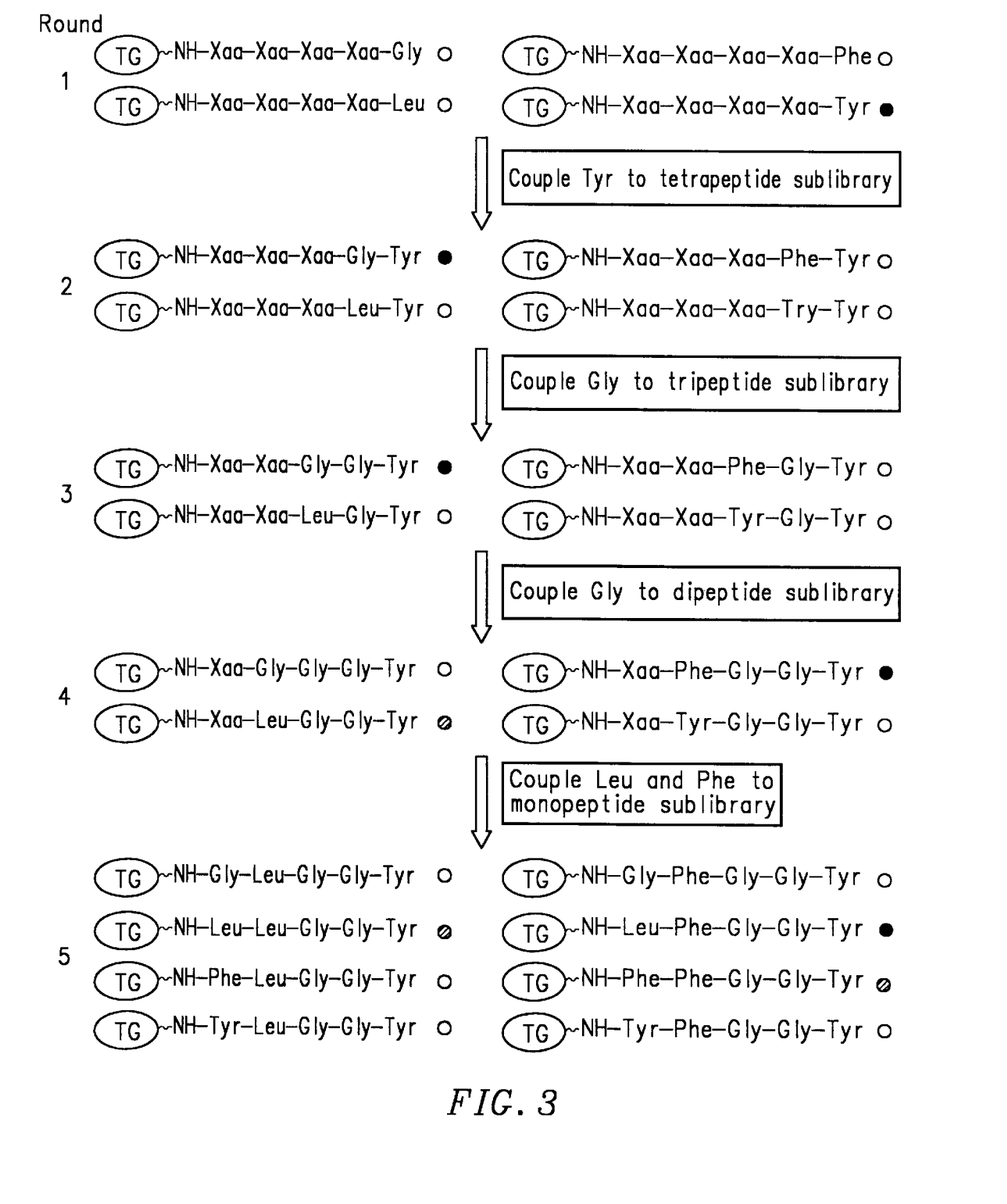
FIG. 3 illustrates the deconvolution of a pentapeptide library.
Figure 4:
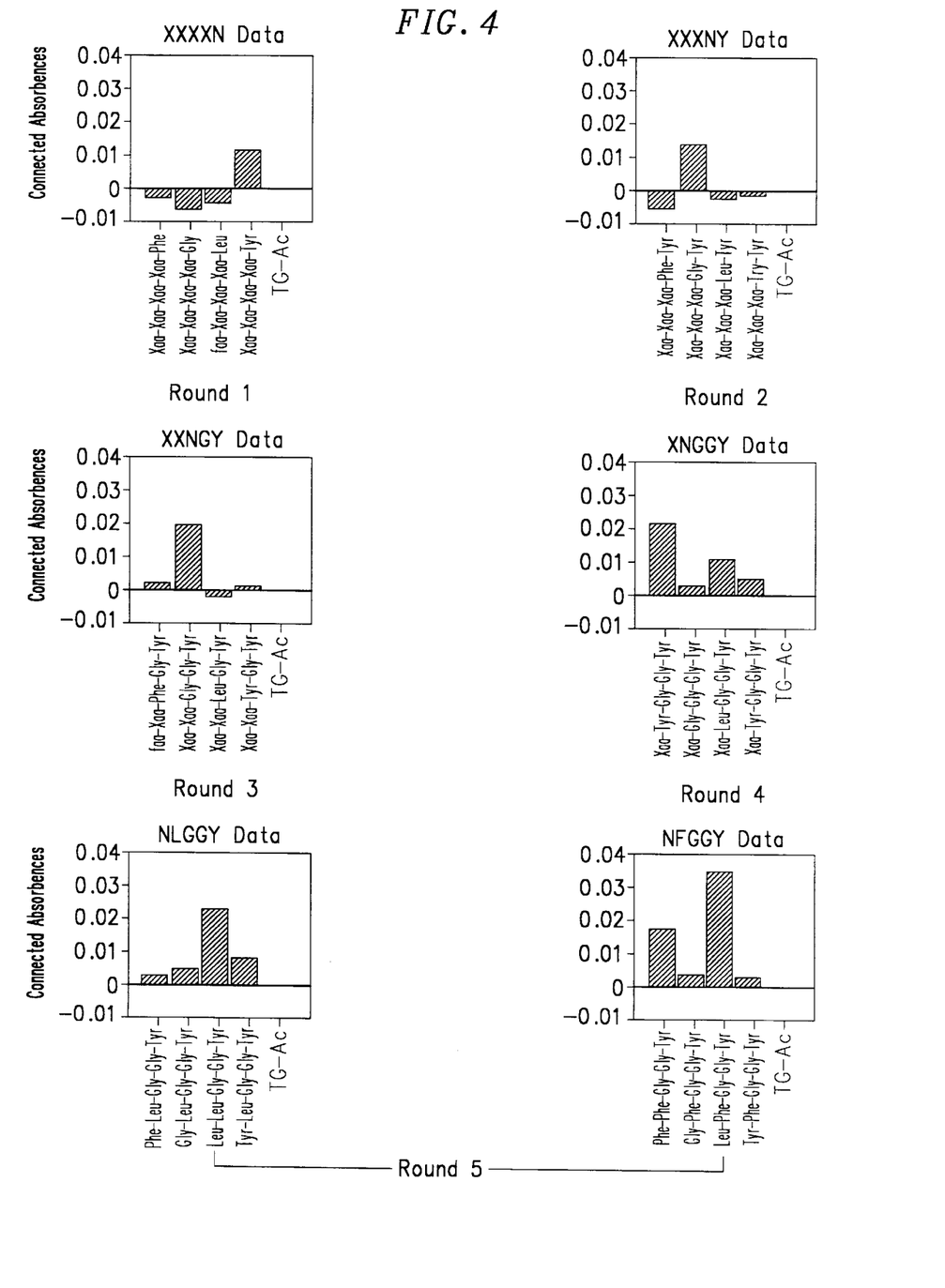
FIG. 4 illustrates the corrected absorbances of pools of library products reacted with β-endorphin antibody to determine the sequence of the pentapeptide which bound best to the β-endorphin antibody.

The binding assays against the β-endorphin antibody were performed with the peptide libraries remaining attached to the Tentagel resin. The deconvolution sequence can be followed pictorially in FIG. 3 showing Scheme 3 and the corrected absorbances for each round are depicted in FIG. 4. In the 4 pools of the pentapeptide libraries, where only the N-terminal amino acid was defined, TG-Xaa-Xaa-Xaa-Xaa-Tyr clearly gave the strongest absorbance. From this point, the 4 tetrapeptide libraries, TG-Xaa-Xaa-Xaa-Gly-FMOC, TG-Xaa-Xaa-Xaa-Leu-FMOC, TG-Xaa-Xaa-Xaa-Phe-FMOC and TG-Xaa-Xaa-Xaa-Tyr-FMOC, saved and labeled during the formation of the pentapeptide combinatorial library, were all coupled with Tyr-FMOC. Of the pools TG-Xaa-Xaa-Xaa-Gly-Tyr, TG-Xaa-Xaa-Xaa-Leu-Tyr, TG-Xaa-Xaa-Xaa-Phe-Tyr, and TG-Xaa-Xaa-Xaa-Tyr-Tyr, TG-Xaa-Xaa-Xaa-Gly-Tyr, obviously gave the strongest binding. This method of deconvolution was repeated to deduce that TG-Xaa-Xaa-Gly-Gly-Tyr was the best binder to the β-endorphin antibody. Solving for the fourth amino acid did not give a clear winner. TG-Xaa-Phe-Gly-Gly-Tyr, the sequence leading to the native epitope to the antibody, was the strongest binder. However, TG-Xaa-Leu-Gly-Gly-Tyr also showed significant binding to the antibody. Significant enough, in fact, to warrant the coupling of Leu-Gly-Gly-Tyr as well as Phe-Gly-Gly-Tyr to the monocoupled Tentagel libraries saved from the first step of the combinatorial synthesis.

In the final analysis, TG-Leu-Phe-Gly-Gly-Tyr, the native epitope, was the most extensive binder. Other weaker binders were also deduced, TG-Phe-Phe-Gly-Gly-Tyr and TG-Leu-Leu-Gly-Gly-Tyr also showed significant binding to the β-endorphin antibody.

Iterative methods of deconvolution have a number of advantages. A variety of chemical libraries, not just peptide or oligonucleotide libraries, can be solved iteratively. An advantage of an iterative deconvolution over encoded libraries is that the use of a decoding tag is avoided. This averts the concern of whether the decoding tag is involved in the binding of a library member to a receptor. Also, an iterative strategy avoids the sensitivity concerns of solving for the active member of a library because iterative methods are not dependent upon sequencing or decoding for the library members bound to a receptor.

Making combinatorial libraries by the split pool method is a cumbersome process. By cataloguing sublibraries along each step of a combinatorial synthesis, only one library needs to be made by the split pool method. While this may not be a tremendous advantage in making libraries that are synthesized in a highly automated manner, like oligonucleotide libraries, in the synthesis of other libraries not yet amenable to automated processes, like small molecule libraries, this iterative method avoids much of the time and labor involved in making split pool libraries for the previous iterative approaches.

SEQUENCE LISTING ( 1 ) GENERAL INFORMATION:

( i i i ) NUMBER OF SEQUENCES: 43

( 2 ) INFORMATION FOR SEQ ID NO: 1:

( i ) SEQUENCE CHARACTERISTICS:
        ( A ) LENGTH: 5
        ( B ) TYPE: amino acid
        ( C ) STRANDEDNESS: single
        ( D ) TOPOLOGY: linear     ( x i ) SEQUENCE DESCRIPTION: SEQ ID NO: 1:

Leu Phe Gly Gly Tyr
1               5

( 2 ) INFORMATION FOR SEQ ID NO: 2:

( i ) SEQUENCE CHARACTERISTICS:
        ( A ) LENGTH: 5
        ( B ) TYPE: amino acid
        ( C ) STRANDEDNESS: single
        ( D ) TOPOLOGY: linear     ( i x ) FEATURE:
        ( D ) OTHER INFORMATION:
            Xaa in location 1, 2, 3, and 4 is any one of the
            amino acids included in the combinatorial library
            amino acid pool.

( x i ) SEQUENCE DESCRIPTION: SEQ ID NO: 2:

Xaa Xaa Xaa Xaa Tyr
1               5

( 2 ) INFORMATION FOR SEQ ID NO: 3:

( i ) SEQUENCE CHARACTERISTICS:
        ( A ) LENGTH: 4
        ( B ) TYPE: amino acid
        ( C ) STRANDEDNESS: single
        ( D ) TOPOLOGY: linear     ( i x ) FEATURE:
        ( D ) OTHER INFORMATION:
            Xaa in location 1, 2 and 3 is any one of the
            amino acids included in the combinatorial library
            amino acid pool.

( x i ) SEQUENCE DESCRIPTION: SEQ ID NO: 3:

Xaa Xaa Xaa Gly
1

( 2 ) INFORMATION FOR SEQ ID NO: 4:

( i ) SEQUENCE CHARACTERISTICS:
        ( A ) LENGTH: 4
        ( B ) TYPE: amino acid
        ( C ) STRANDEDNESS: single
        ( D ) TOPOLOGY: linear     ( i x ) FEATURE:
        ( D ) OTHER INFORMATION:
            Xaa in location 1, 2 and 3 is any one of the
            amino acids included in the combinatorial library
            amino acid pool.

( x i ) SEQUENCE DESCRIPTION: SEQ ID NO: 4:

Xaa Xaa Xaa Leu
1

( 2 ) INFORMATION FOR SEQ ID NO: 5:

( i ) SEQUENCE CHARACTERISTICS:
        ( A ) LENGTH: 4
        ( B ) TYPE: amino acid
        ( C ) STRANDEDNESS: single
        ( D ) TOPOLOGY: linear     ( i x ) FEATURE:
        ( D ) OTHER INFORMATION:
            Xaa in location 1, 2 and 3 is any one of the
            amino acids included in the combinatorial library
            amino acid pool.

( x i ) SEQUENCE DESCRIPTION: SEQ ID NO: 5:

Xaa Xaa Xaa Phe
1

( 2 ) INFORMATION FOR SEQ ID NO: 6:

( i ) SEQUENCE CHARACTERISTICS:
        ( A ) LENGTH: 4
        ( B ) TYPE: amino acid
        ( C ) STRANDEDNESS: single
        ( D ) TOPOLOGY: linear     ( i x ) FEATURE:
        ( D ) OTHER INFORMATION:
            Xaa in location 1, 2 and 3 is any one of the
            amino acids included in the combinatorial library
            amino acid pool.

( x i ) SEQUENCE DESCRIPTION: SEQ ID NO: 6:

Xaa Xaa Xaa Tyr
1

( 2 ) INFORMATION FOR SEQ ID NO: 7:

( i ) SEQUENCE CHARACTERISTICS:
        ( A ) LENGTH: 5
        ( B ) TYPE: amino acid
        ( C ) STRANDEDNESS: single
        ( D ) TOPOLOGY: linear     ( i x ) FEATURE:
        ( D ) OTHER INFORMATION:
            Xaa in location 1, 2 and 3 is any one of the
            amino acids included in the combinatorial library
            amino acid pool.

( x i ) SEQUENCE DESCRIPTION: SEQ ID NO: 7:

Xaa Xaa Xaa Gly Tyr
1                    5

( 2 ) INFORMATION FOR SEQ ID NO: 8:

( i ) SEQUENCE CHARACTERISTICS:
        ( A ) LENGTH: 5
        ( B ) TYPE: amino acid
        ( C ) STRANDEDNESS: single
        ( D ) TOPOLOGY: linear     ( i x ) FEATURE:
        ( D ) OTHER INFORMATION:
            Xaa in location 1, 2 and 3 is any one of the
            amino acids included in the combinatorial library
            amino acid pool.

( x i ) SEQUENCE DESCRIPTION: SEQ ID NO: 8:

Xaa Xaa Xaa Leu Tyr
1                    5

( 2 ) INFORMATION FOR SEQ ID NO: 9:

( i ) SEQUENCE CHARACTERISTICS:
        ( A ) LENGTH: 5
        ( B ) TYPE: amino acid
        ( C ) STRANDEDNESS: single
        ( D ) TOPOLOGY: linear     ( i x ) FEATURE:
        ( D ) OTHER INFORMATION:
            Xaa in location 1, 2 and 3 is any one of the
            amino acids included in the combinatorial library
            amino acid pool.

( x i ) SEQUENCE DESCRIPTION: SEQ ID NO: 9:

Xaa Xaa Xaa Phe Tyr
1               5

( 2 ) INFORMATION FOR SEQ ID NO: 10:

( i ) SEQUENCE CHARACTERISTICS:
        ( A ) LENGTH: 5
        ( B ) TYPE: amino acid
        ( C ) STRANDEDNESS: single
        ( D ) TOPOLOGY: linear     ( i x ) FEATURE:
        ( D ) OTHER INFORMATION:
            Xaa in location 1, 2 and 3 is any one of the
            amino acids included in the combinatorial library
            amino acid pool.

( x i ) SEQUENCE DESCRIPTION: SEQ ID NO: 10:

Xaa Xaa Xaa Tyr Tyr
1               5

( 2 ) INFORMATION FOR SEQ ID NO: 11:

( i ) SEQUENCE CHARACTERISTICS:
        ( A ) LENGTH: 5
        ( B ) TYPE: amino acid
        ( C ) STRANDEDNESS: single
        ( D ) TOPOLOGY: linear     ( i x ) FEATURE:
        ( D ) OTHER INFORMATION:
            Xaa in location 1, 2 and 3 is any one of the
            amino acids included in the combinatorial library
            amino acid pool.

( x i ) SEQUENCE DESCRIPTION: SEQ ID NO: 11:

Xaa Xaa Xaa Gly Tyr
1               5

( 2 ) INFORMATION FOR SEQ ID NO: 12:

( i ) SEQUENCE CHARACTERISTICS:
        ( A ) LENGTH: 5
        ( B ) TYPE: amino acid
        ( C ) STRANDEDNESS: single
        ( D ) TOPOLOGY: linear     ( i x ) FEATURE:
        ( D ) OTHER INFORMATION:
            Xaa in location 1 and 2 is any one of the
            amino acids included in the combinatorial library
            amino acid pool.

( x i ) SEQUENCE DESCRIPTION: SEQ ID NO: 12:

Xaa Xaa Gly Gly Tyr
1               5

( 2 ) INFORMATION FOR SEQ ID NO: 13:

( i ) SEQUENCE CHARACTERISTICS:
        ( A ) LENGTH: 5
        ( B ) TYPE: amino acid
        ( C ) STRANDEDNESS: single
        ( D ) TOPOLOGY: linear     ( i x ) FEATURE:
        ( D ) OTHER INFORMATION:
            Xaa in location 1 is any one of the
            amino acids included in the combinatorial library
            amino acid pool.

( x i ) SEQUENCE DESCRIPTION: SEQ ID NO: 13:

Xaa Phe Gly Gly Tyr
1               5

( 2 ) INFORMATION FOR SEQ ID NO: 14:

( i ) SEQUENCE CHARACTERISTICS:
        ( A ) LENGTH: 5
        ( B ) TYPE: amino acid
        ( C ) STRANDEDNESS: single
        ( D ) TOPOLOGY: linear     ( i x ) FEATURE:
        ( D ) OTHER INFORMATION:
            Xaa in location 1 is any one of the
            amino acids included in the combinatorial library
            amino acid pool.

( x i ) SEQUENCE DESCRIPTION: SEQ ID NO: 14:

Xaa Leu Gly Gly Tyr
1               5

( 2 ) INFORMATION FOR SEQ ID NO: 15:

( i ) SEQUENCE CHARACTERISTICS:
        ( A ) LENGTH: 4
        ( B ) TYPE: amino acid
        ( C ) STRANDEDNESS: single
        ( D ) TOPOLOGY: linear     ( x i ) SEQUENCE DESCRIPTION: SEQ ID NO: 15:

Leu Gly Gly Tyr
1

( 2 ) INFORMATION FOR SEQ ID NO: 16:

( i ) SEQUENCE CHARACTERISTICS:
        ( A ) LENGTH: 4
        ( B ) TYPE: amino acid
        ( C ) STRANDEDNESS: single
        ( D ) TOPOLOGY: linear     ( x i ) SEQUENCE DESCRIPTION: SEQ ID NO: 16:

Phe Gly Gly Tyr
1

( 2 ) INFORMATION FOR SEQ ID NO: 17:

( i ) SEQUENCE CHARACTERISTICS:
        ( A ) LENGTH: 5
        ( B ) TYPE: amino acid
        ( C ) STRANDEDNESS: single
        ( D ) TOPOLOGY: linear     ( x i ) SEQUENCE DESCRIPTION: SEQ ID NO: 17:

Leu Phe Gly Gly Tyr ( 2 ) INFORMATION FOR SEQ ID NO: 18:

( i ) SEQUENCE CHARACTERISTICS:
        ( A ) LENGTH: 5
        ( B ) TYPE: amino acid
        ( C ) STRANDEDNESS: single
        ( D ) TOPOLOGY: linear     ( x i ) SEQUENCE DESCRIPTION: SEQ ID NO: 18:

Phe Phe Gly Gly Tyr ( 2 ) INFORMATION FOR SEQ ID NO: 19:

( i ) SEQUENCE CHARACTERISTICS:
        ( A ) LENGTH: 5
        ( B ) TYPE: amino acid
        ( C ) STRANDEDNESS: single
        ( D ) TOPOLOGY: linear     ( x i ) SEQUENCE DESCRIPTION: SEQ ID NO: 19:

Leu Leu Gly Gly Tyr ( 2 ) INFORMATION FOR SEQ ID NO: 20:

( i ) SEQUENCE CHARACTERISTICS:
        ( A ) LENGTH: 5
        ( B ) TYPE: amino acid
        ( C ) STRANDEDNESS: single
        ( D ) TOPOLOGY: linear     ( i x ) FEATURE:
        ( D ) OTHER INFORMATION:
            Xaa in location 1, 2, 3, and 4 is any one of the
            amino acids included in the combinatorial library
            amino acid pool.

( x i ) SEQUENCE DESCRIPTION: SEQ ID NO: 20:

Xaa Xaa Xaa Xaa Gly
1                        5

( 2 ) INFORMATION FOR SEQ ID NO: 21:

( i ) SEQUENCE CHARACTERISTICS:
        ( A ) LENGTH: 5
        ( B ) TYPE: amino acid
        ( C ) STRANDEDNESS: single
        ( D ) TOPOLOGY: linear     ( i x ) FEATURE:
        ( D ) OTHER INFORMATION:
            Xaa in location 1, 2, 3, and 4 is any one of the
            amino acids included in the combinatorial library
            amino acid pool.

( x i ) SEQUENCE DESCRIPTION: SEQ ID NO: 21:

Xaa Xaa Xaa Xaa Leu
1                        5

( 2 ) INFORMATION FOR SEQ ID NO: 22:

( i ) SEQUENCE CHARACTERISTICS:
        ( A ) LENGTH: 5
        ( B ) TYPE: amino acid
        ( C ) STRANDEDNESS: single
        ( D ) TOPOLOGY: linear     ( i x ) FEATURE:
        ( D ) OTHER INFORMATION:
            Xaa in location 1, 2 and 3 is any one of the amino acids included in the combinatorial library
amino acid pool.

(x i) SEQUENCE DESCRIPTION: SEQ ID NO: 22:

Xaa Xaa Xaa Gly Tyr
1               5

(2) INFORMATION FOR SEQ ID NO: 23:

(i) SEQUENCE CHARACTERISTICS:
  (A) LENGTH: 5
  (B) TYPE: amino acid
  (C) STRANDEDNESS: single
  (D) TOPOLOGY: linear (i x) FEATURE:
  (D) OTHER INFORMATION:
      Xaa in location 1, 2 and 3 is any one of the
      amino acids included in the combinatorial library
      amino acid pool.

(x i) SEQUENCE DESCRIPTION: SEQ ID NO: 23:

Xaa Xaa Xaa Leu Tyr
1               5

(2) INFORMATION FOR SEQ ID NO: 24:

(i) SEQUENCE CHARACTERISTICS:
  (A) LENGTH: 5
  (B) TYPE: amino acid
  (C) STRANDEDNESS: single
  (D) TOPOLOGY: linear (i x) FEATURE:
  (D) OTHER INFORMATION:
      Xaa in location 1 and 2 is any one of the
      amino acids included in the combinatorial library
      amino acid pool.

(x i) SEQUENCE DESCRIPTION: SEQ ID NO: 24:

Xaa Xaa Gly Gly Tyr
1               5

(2) INFORMATION FOR SEQ ID NO: 25:

(i) SEQUENCE CHARACTERISTICS:
  (A) LENGTH: 5
  (B) TYPE: amino acid
  (C) STRANDEDNESS: single
  (D) TOPOLOGY: linear (i x) FEATURE:
  (D) OTHER INFORMATION:
      Xaa in location 1 and 2 is any one of the
      amino acids included in the combinatorial library
      amino acid pool.

(x i) SEQUENCE DESCRIPTION: SEQ ID NO: 25:

Xaa Xaa Leu Gly Tyr
1               5

(2) INFORMATION FOR SEQ ID NO: 26:

(i) SEQUENCE CHARACTERISTICS:
  (A) LENGTH: 5
  (B) TYPE: amino acid
  (C) STRANDEDNESS: single
  (D) TOPOLOGY: linear (i x) FEATURE:
  (D) OTHER INFORMATION:
      Xaa in location 1 is any one of the amino acids included in the combinatorial library
amino acid pool.

( x i ) SEQUENCE DESCRIPTION: SEQ ID NO: 26:

Xaa  Gly  Gly  Gly  Tyr
1                    5

( 2 ) INFORMATION FOR SEQ ID NO: 27:

( i ) SEQUENCE CHARACTERISTICS:
        ( A ) LENGTH: 5
        ( B ) TYPE: amino acid
        ( C ) STRANDEDNESS: single
        ( D ) TOPOLOGY: linear     ( i x ) FEATURE:
        ( D ) OTHER INFORMATION:
            Xaa in location 1 is any one of the
            amino acids included in the combinatorial library
            amino acid pool.

( x i ) SEQUENCE DESCRIPTION: SEQ ID NO: 27:

Xaa  Leu  Gly  Gly  Tyr
1                    5

( 2 ) INFORMATION FOR SEQ ID NO: 28:

( i ) SEQUENCE CHARACTERISTICS:
        ( A ) LENGTH: 5
        ( B ) TYPE: amino acid
        ( C ) STRANDEDNESS: single
        ( D ) TOPOLOGY: linear     ( x i ) SEQUENCE DESCRIPTION: SEQ ID NO: 28:

Gly  Leu  Gly  Gly  Tyr
1                    5

( 2 ) INFORMATION FOR SEQ ID NO: 29:

( i ) SEQUENCE CHARACTERISTICS:
        ( A ) LENGTH: 5
        ( B ) TYPE: amino acid
        ( C ) STRANDEDNESS: single
        ( D ) TOPOLOGY: linear     ( x i ) SEQUENCE DESCRIPTION: SEQ ID NO: 29:

Leu  Leu  Gly  Gly  Tyr
1                    5

( 2 ) INFORMATION FOR SEQ ID NO: 30:

( i ) SEQUENCE CHARACTERISTICS:
        ( A ) LENGTH: 5
        ( B ) TYPE: amino acid
        ( C ) STRANDEDNESS: single
        ( D ) TOPOLOGY: linear     ( x i ) SEQUENCE DESCRIPTION: SEQ ID NO: 30:

Phe  Leu  Gly  Gly  Tyr
1                    5

( 2 ) INFORMATION FOR SEQ ID NO: 31:

( i ) SEQUENCE CHARACTERISTICS:
        ( A ) LENGTH: 5
        ( B ) TYPE: amino acid
        ( C ) STRANDEDNESS: single
        ( D ) TOPOLOGY: linear     ( x i ) SEQUENCE DESCRIPTION: SEQ ID NO: 31:

Tyr Leu Gly Gly Tyr
1               5

(2) INFORMATION FOR SEQ ID NO: 32:

(i) SEQUENCE CHARACTERISTICS:
        (A) LENGTH: 5
        (B) TYPE: amino acid
        (C) STRANDEDNESS: single
        (D) TOPOLOGY: linear     (ix) FEATURE:
        (D) OTHER INFORMATION:
            Xaa in location 1, 2, 3, and 4 is any one of the
            amino acids included in the combinatorial library
            amino acid pool.

(xi) SEQUENCE DESCRIPTION: SEQ ID NO: 32:

Xaa Xaa Xaa Xaa Phe
1               5

(2) INFORMATION FOR SEQ ID NO: 33:

(i) SEQUENCE CHARACTERISTICS:
        (A) LENGTH: 5
        (B) TYPE: amino acid
        (C) STRANDEDNESS: single
        (D) TOPOLOGY: linear     (ix) FEATURE:
        (D) OTHER INFORMATION:
            Xaa in location 1, 2, 3, and 4 is any one of the
            amino acids included in the combinatorial library
            amino acid pool.

(xi) SEQUENCE DESCRIPTION: SEQ ID NO: 33:

Xaa Xaa Xaa Xaa Tyr
1               5

(2) INFORMATION FOR SEQ ID NO: 34:

(i) SEQUENCE CHARACTERISTICS:
        (A) LENGTH: 5
        (B) TYPE: amino acid
        (C) STRANDEDNESS: single
        (D) TOPOLOGY: linear     (ix) FEATURE:
        (D) OTHER INFORMATION:
            Xaa in location 1, 2 and 3 is any one of the
            amino acids included in the combinatorial library
            amino acid pool.

(xi) SEQUENCE DESCRIPTION: SEQ ID NO: 34:

Xaa Xaa Xaa Phe Tyr
1               5

(2) INFORMATION FOR SEQ ID NO: 35:

(i) SEQUENCE CHARACTERISTICS:
        (A) LENGTH: 5
        (B) TYPE: amino acid
        (C) STRANDEDNESS: single
        (D) TOPOLOGY: linear     (ix) FEATURE:
        (D) OTHER INFORMATION:
            Xaa in location 1, 2 and 3 is any one of the
            amino acids included in the combinatorial library
            amino acid pool.

(xi) SEQUENCE DESCRIPTION: SEQ ID NO: 35:

Xaa Xaa Xaa Tyr Tyr
1               5

(2) INFORMATION FOR SEQ ID NO: 36:

(i) SEQUENCE CHARACTERISTICS:
        (A) LENGTH: 5
        (B) TYPE: amino acid
        (C) STRANDEDNESS: single
        (D) TOPOLOGY: linear     (ix) FEATURE:
        (D) OTHER INFORMATION:
            Xaa in location 1 and 2 is any one of the
            amino acids included in the combinatorial library
            amino acid pool.

(xi) SEQUENCE DESCRIPTION: SEQ ID NO: 36:

Xaa Xaa Phe Gly Tyr
1               5

(2) INFORMATION FOR SEQ ID NO: 37:

(i) SEQUENCE CHARACTERISTICS:
        (A) LENGTH: 5
        (B) TYPE: amino acid
        (C) STRANDEDNESS: single
        (D) TOPOLOGY: linear     (ix) FEATURE:
        (D) OTHER INFORMATION:
            Xaa in location 1 and 2 is any one of the
            amino acids included in the combinatorial library
            amino acid pool.

(xi) SEQUENCE DESCRIPTION: SEQ ID NO: 37:

Xaa Xaa Tyr Gly Tyr
1               5

(2) INFORMATION FOR SEQ ID NO: 38:

(i) SEQUENCE CHARACTERISTICS:
        (A) LENGTH: 5
        (B) TYPE: amino acid
        (C) STRANDEDNESS: single
        (D) TOPOLOGY: linear     (ix) FEATURE:
        (D) OTHER INFORMATION:
            Xaa in location 1 is any one of the amino acids
            included in the combinatorial library amino acid
            pool.

(xi) SEQUENCE DESCRIPTION: SEQ ID NO: 38:

Xaa Phe Gly Gly Tyr
1               5

(2) INFORMATION FOR SEQ ID NO: 39:

(i) SEQUENCE CHARACTERISTICS:
        (A) LENGTH: 5
        (B) TYPE: amino acid
        (C) STRANDEDNESS: single
        (D) TOPOLOGY: linear     (ix) FEATURE:
        (D) OTHER INFORMATION:
            Xaa in location 1 is any one of the amino acids
            included in the combinatorial library amino acid
            pool.

(xi) SEQUENCE DESCRIPTION: SEQ ID NO: 39:

```
Xaa  Tyr  Gly  Gly  Tyr
1                      5
```

( 2 ) INFORMATION FOR SEQ ID NO: 40:

( i ) SEQUENCE CHARACTERISTICS:
        ( A ) LENGTH: 5
        ( B ) TYPE: amino acid
        ( C ) STRANDEDNESS: single
        ( D ) TOPOLOGY: linear     ( x i ) SEQUENCE DESCRIPTION: SEQ ID NO: 40:

```
Gly  Phe  Gly  Gly  Tyr
1                      5
```

( 2 ) INFORMATION FOR SEQ ID NO: 41:

( i ) SEQUENCE CHARACTERISTICS:
        ( A ) LENGTH: 5
        ( B ) TYPE: amino acid
        ( C ) STRANDEDNESS: single
        ( D ) TOPOLOGY: linear     ( x i ) SEQUENCE DESCRIPTION: SEQ ID NO: 41:

```
Leu  Phe  Gly  Gly  Tyr
1                      5
```

( 2 ) INFORMATION FOR SEQ ID NO: 42:

( i ) SEQUENCE CHARACTERISTICS:
        ( A ) LENGTH: 5
        ( B ) TYPE: amino acid
        ( C ) STRANDEDNESS: single
        ( D ) TOPOLOGY: linear     ( x i ) SEQUENCE DESCRIPTION: SEQ ID NO: 42:

```
Phe  Phe  Gly  Gly  Tyr
1                      5
```

( 2 ) INFORMATION FOR SEQ ID NO: 43:

( i ) SEQUENCE CHARACTERISTICS:
        ( A ) LENGTH: 5
        ( B ) TYPE: amino acid
        ( C ) STRANDEDNESS: single
        ( D ) TOPOLOGY: linear     ( x i ) SEQUENCE DESCRIPTION: SEQ ID NO: 43:

```
Tyr  Phe  Gly  Gly  Tyr
1                      5
```

I claim:

1. Method for construction of a kit useful for identification of a desired compound, comprising the steps of:
- (a) providing a first plurality of vessels comprising different polysubunits each constructed from a known number of subunits joined together by one or more bonds, wherein each said subunit and bond can be the same or different, each said different polysubunit comprising a different sequence of subunits but having the same known subunit at one terminus of said polysubunit each said vessel comprising polysubunits having a different known subunit at said terminus,
- (b) combining aliquots of said different polysubunits from each said vessel to form a mixture, wherein said aliquots are less than all of the contents of each said vessel,
- (c) retaining at least a portion of the remaining contents of each said vessel as separate aliquots,
- (d) dividing said mixture into a second plurality of vessels, and
- (e) bonding a further subunit to each said terminus of each said polysubunit in said second plurality of vessels; wherein said subunit is different for each said second plurality of vessels, and wherein each said polysubunit in said second plurality of vessels differs from each said polysubunit in each first plurality of vessels by the presence of an extra subunit.

2. The method of claim 1, wherein said method further comprises repeating said steps (a) through (d) for said second plurality of vessels.

3. The method of claim 2, comprising repeating said steps (a) through (d) a plurality of times.

4. Method for identification of a desired compound, comprising the steps of:

(a) providing a kit comprising a first and second plurality of vessels, said first plurality of vessels comprising different polysubunits, each constructed from a known number of subunits joined together by one or more bonds, wherein each said subunit and bond can be the same or different, each said different polysubunit comprising a different sequence of subunits but having the same known subunit at one terminus of said polysubunit, each one of said first plurality of vessels comprising polysubunits having a different known subunit at said terminus, and said second plurality of vessels comprising different polysubunits, each constructed from said known number of subunits minus one subunit, joined together by one or more bonds, wherein each said subunit and bond can be the same or different, each said different polysubunit comprising a different sequence of subunits but having the same known subunit at one terminus of said polysubunit, each one of said second plurality of vessels comprising polysubunits having a different known subunit at said terminus, and screening said first plurality of vessels to identify a vessel having a desired activity in an assay, and thereby identifying a first known subunit;

(b) coupling said first known subunit to a terminus of an aliquot of the contents of each of said different polysubunits in said second plurality of vessels; and (c) screening said different polysubunits comprising said first known subunit for said desired activity in said assay, and thereby identifying a second known subunit.

5. The method of claim 4, wherein said steps (a) and (b) are repeated a plurality of times.

* * * * *